US011690361B2

(12) United States Patent
Dattilo et al.

(10) Patent No.: US 11,690,361 B2
(45) Date of Patent: Jul. 4, 2023

(54) TRANSITION COW INDEX (71) Applicant: GENUS PLC, DeForest, WI (US)

(72) Inventors: Katrina Dattilo, DeForest, WI (US); Yalda Zare, DeForest, WI (US); Gabriela Marquez Betz, DeForest, WI (US); Kaleena Stephan, DeForest, WI (US); Ryan Starkenburg, DeForest, WI (US); Cristian Vergara, DeForest, WI (US)

(73) Assignee: ABS Global, Inc., DeForest, WI (US)

( * ) Notice: Subject to any disclaimer, the term of this patent is extended or adjusted under 35 U.S.C. 154(b) by 1050 days.

(21) Appl. No.: 16/445,832

(22) Filed: Jun. 19, 2019

(65) Prior Publication Data
US 2019/0357504 A1 Nov. 28, 2019

Related U.S. Application Data (63) Continuation of application No. 15/224,336, filed on Jul. 29, 2016, now Pat. No. 10,368,532.

(60) Provisional application No. 62/350,813, filed on Jun. 16, 2016, provisional application No. 62/198,455, filed on Jul. 29, 2015.

(51) Int. Cl.
A01K 67/02 (2006.01)
G16B 20/40 (2019.01)
G16B 20/20 (2019.01)
G16H 50/30 (2018.01)
G16B 20/00 (2019.01)
A61D 19/04 (2006.01)

(52) U.S. Cl.
CPC .............. A01K 67/02 (2013.01); A61D 19/04 (2013.01); G16B 20/00 (2019.02); G16B 20/20 (2019.02); G16B 20/40 (2019.02); G16H 50/30 (2018.01); A01K 2227/101 (2013.01)

(58) Field of Classification Search
None
See application file for complete search history.

(56) References Cited

U.S. PATENT DOCUMENTS

| | | | |
|---|---|---|---|
| 10,368,532 B2 * | 8/2019 | Dattilo | G16B 20/20 |
| 2002/0102601 A1 | 8/2002 | Fitzpatrick et al. | |
| 2004/0241723 A1 | 12/2004 | Marquess et al. | |
| 2005/0123929 A1 | 6/2005 | Khatib | |
| 2005/0153317 A1 | 7/2005 | DeNise et al. | |
| 2005/0221322 A1 | 10/2005 | Fox | |
| 2006/0058273 A1 | 3/2006 | Cox et al. | |
| 2007/0026493 A1 | 2/2007 | Paszek et al. | |
| 2007/0056516 A1 | 3/2007 | Nordlund et al. | |
| 2008/0189085 A1 | 8/2008 | Cook et al. | |
| 2012/0004112 A1 | 1/2012 | Lund et al. | |
| 2013/0040902 A1 | 2/2013 | Miron et al. | |
| 2013/0316031 A1 | 11/2013 | Kaneda et al. | |
| 2015/0240308 A1 * | 8/2015 | Guldbrandtsen | C12Q 1/6883 506/9 |
| 2016/0165922 A1 | 6/2016 | Pozo et al. | |
| 2016/0309685 A1 | 10/2016 | Lightner et al. | |

FOREIGN PATENT DOCUMENTS

AU 2010202253 C1 * 11/2020 ........... C12Q 1/6827

OTHER PUBLICATIONS

Simm G, Oldham JD, Coffey MP. Dairy cows in the future. BSAP Occasional Publication. 2001;26(1):1-8. (Year: 2001).*
Presicce GA, Xu J, Gong G, Moreno JF, Chaubal S, Xue F, Bella A, Senatore EM, Yang X, Tian XC, Du F. Oocyte source and hormonal stimulation for in vitro fertilization using sexed spermatozoa in cattle. Veterinary medicine international. Sep. 5, 2011;2011 (Year: 2011).*
Thomas MG, Williams GL. Metabolic hormone secretion and FSH-induced superovulatory responses of beef heifers fed dietary fat supplements containing predominantly saturated or polyunsaturated fatty acids. Theriogenology. Jan. 15, 1996;45(2):451-8 (Year: 1996).*
Bouquet A, Juga J. Integrating genomic selection into dairy cattle breeding programmes: a review. Animal. May 2013;7(5):705-13. (Year: 2013).*
Chandra V, Sejian V, Sharma GT. Strategies to improve livestock reproduction under the changing climate scenario. In Climate change impacton livestock: adaptation and mitigation 2015 (pp. 425-439). Springer, New Delhi (Year: 2015).*
Pryce JE, Daetwyler HD. Designing dairy cattle breeding schemes under genomic selection: a review of international research. Animal Production Science. Dec. 9, 2011;52(3):107-14 (Year: 2011).*
Hayakawa H, Hirai T, Takimoto A, Ideta A, Aoyagi Y. Superovulation and embryo transfer in Holstein cattle using sexed sperm. Theriogenology. Jan. 1, 2009;71(1):68-73. (Year: 2009).*
Stear M, Nikbakht G, Matthews L, Jonsson N. Breeding for disease resistance in livestock and fish. Anim Sci Rev. 2012;7:1-10. (Year: 2012).*
Bareille et al., "Effects of health disorders on feed intake and milk production in dairy cows", Livestock Production Science, vol. 83, Issue 1, pp. 53-62, Sep. 2003.

(Continued)

Primary Examiner — Michael D Burkhart
(74) Attorney, Agent, or Firm — McKee, Voorhees & Sease, PLC (57) ABSTRACT Applicants have identified that three critical phenotypic/genetic measures are highly correlated with transition period health and may be used in selection and breeding protocols and/or in combination with traditional breeding and marker assisted selection methods to improve predictability of transition period health. According to the invention genetic evaluations for mastitis, ketosis, and metritis have been found to be highly predictive of overall transition health. The genetic evaluations are produced by directly measuring thousands of clinical cases of mastitis, ketosis, and metritis in ancestors of a particular animal and using this data in selection. Applicant's selection criteria and quickly impact a breeders population by reducing transition cow disease incidence in the initial population and in progeny.

20 Claims, 5 Drawing Sheets (56) References Cited

OTHER PUBLICATIONS

Cole et al., "Genomic evaluation of health traits in dairy cattle", International Committee on Animal Recording (ICAR). Technical Series 17:167-175, retrieved from: https://www.icar.org/documents/aarhus_2013/Manuscripts/Cole.pdf, 9 pages, 2013.

Koeck et al., "Health recording in Canadian Holsteins: Data and genetic parameters", J. Dairy Sci., vol. 95, pp. 4099-4108, Feb. 18, 2012.

Zwald et al., "Genetic Selection for Health Traits Using Producer-Recorded Data. I. Incidence Rates, Heritability Estimates, and Sire Breeding Values", J. Dairy Sci., vol. 87, pp. 4287-4294, Sep. 10, 2004.

Appuhamy et al., "Phenotypic and Genetic Relationships of Common Health Disorders with Milk and Fat Yield Persistencies from Producer-Recorded Health Data and Test-Day Yields" J. Dairy Science, 92: pp. 1785-1795 2009.

Congleton, Jr et al., "Profitability of Dairy Cow Herd Life", J. Dairy Science, 7: pp. 661-674, 1984.

Deluyker et al., "Change of Milk Yield with Clinical Diseases for a High Producing Dairy Herd", J. Dairy Science, American Dairy Science Association, U.S., vol. 74, No. 2, pp. 436-445, 1991.

Fleischer et al., The Relationship Between Milk Yield and the Incidence of Some Diseases in Dairy Cows, J. Dairy Science, 84: pp. 2025-2035, 2001.

Gaddis et al., "Genomic Prediction of Disease Occurrence Using Producer-Recorded Health Data: A Comparison of Methods" Genetics Selection Evolution, 14 pages, 2015.

Nash et al., "Heritability of Clinical Mastitis Incidence and Relationships with Sire Transmitting Abilities for Somatic Cell Score, Udder Type Traits, Productive Life, and Protein Yield", J. Dairy Science, 83: pp. 2350-2360, 2000.

Genus, PLC, PCT/US2016/044824 filed Jul. 29, 2016, "The International Search Report and the Written Opinion of tie International Searching Authority, or the Declaration", 16 pages, dated Nov. 30, 2016.

Aguilar et al., "Hot Topic: A Unified Approach to Utilize Phenotypic, Full Pedigree, and Genomic Information for Genetic Evaluation of Holstein Final Score", J. Dairy Sci., 93, pp. 743-752, 2010.

Fernando et al., "A Class of Bayesian Methods to Combine Large Numbers of Genotyped and Non-Genotyped Animals for Whole-Genome Analyses", Genetics Selection Evolution, 46:50, 13 pages, 2014.

Henderson, C.R., "Best Linear Unbiased Estimation and Prediction Under a Selection Model", Biometrics, vol. 31, No. 2, pp. 423-447, Jun. 1975.

Meuwissen et al., "Prediction of Total Genetic Value Using Genome-Wide Dense Marker Maps", Genetics, 157: pp. 1819-1829, Jan. 17, 2001.

Gilmour et al., ASReml User Guide, Release 4.1, Structural Specification, 366 pages, Dec. 22, 2014.

Vanraden, P.M., "Efficient Methods to Compute Genomic Predictions", J. Dairy Sci., 91, pp. 4414-4423, 2008.

Tanana et al., "Principles of breeding livestock, A study guide for students of the Faculty of Advanced Training and Staff Retraining and student's individual work of full-time and distance education form for occupation 1-740301", Animal Science, 5 pages, 2011.

Zavadilova et al., "Genetic analysis of clinical mastitis data for Holstein cattle in the Czech Republic", Arch. Anim. Breed., vol. 58, pp. 199-204, May 21, 2015.

\* cited by examiner

TRANSITION COW INDEX

CROSS REFERENCE TO RELATED APPLICATION

This application is a Continuation Application of U.S. Ser. No. 15/224,336, filed Jul. 29, 2016, which claims priority under 35 U.S.C. § 119 to provisional applications U.S. Ser. No. 62/198,455 filed Jul. 29, 2015, and 62/350,813 filed Jun. 16, 2016, which are herein incorporated by reference in their entirety.

FIELD OF THE INVENTION

The present invention relates to selection and breeding methods and resultant progeny and populations of cattle with improved milk production traits, including milk yield and milk composition, as well as transition to lactation.

BACKGROUND OF THE INVENTION

Each dairy producer globally is faced with challenges of transitioning each female that enters the milking string from pregnant to calving and ultimately efficiently produce enough milk to generate profit. In a year, farmers can lose up to 10% of their herds in the two months following calving due to health issues. Indeed, 75% of disease in dairy cows occurs in the first 60 days after a lactation begins with as much as 50% of high producing cows affected. Compounding the significance of ensuring healthy transition for cows is the economic commitment to treating transition period diseases. The cost per disease case per lactation is between $200 to $400 for each disease incidence. The total annual economic loss due to Metritis alone, in a dairy herd with 1,000 cows and an average disease incidence of 15% could reach up to $53,000, representing a significant economic burden.

The transition period is critical as the first and over-riding priority of a pregnant cow's body is to make milk, even at the expense of her own health. She will use her own energy reserves resulting in a negative energy balance which can have a negative impact on her short and long-term health. This is exacerbated by the cow's immune system suppression resulting from the pregnancy. Because of this behavior, and contrary to traditional logic, low milk production is not necessarily an indicator a cow has developed or is susceptible to a health issue during this period since a cow that does not transition well often is still a good milk producer.

Farmers have done their best to prevent and react to health issues that arise during the transition cow period with the tools available. As new management, animal health, and nutrition tools have been introduced, farmers have invested in them eagerly in hopes of minimizing the negative impact of health issues related to this transition period in each cow's life. Unfortunately the gains are generally temporary and the farmer must re-invest in the tools each time a cow goes through this period. Thus, there remains a need in the art for breeders to effectively minimize the need for additional preventative and reactionary measures while reducing the negative health issues a cow is susceptible to during the transition period. According to the invention, breeders can now change their approach and start selecting genetics for their herds demonstrated to effectively minimize the need for additional preventive and reactionary measures to transition cow health issues such as mastitis, metritis, and ketosis. Genetic selection is a cumulative and cost effective way to make permanent change to the herd so as to not have to rely on the cycle of prevention and treatment currently utilized.

Traditional breeding techniques involve the studying of sire progenies, and evaluating their milk production ratings (breeding values, or genetic merit) to guide further breeding. This standard technique requires years to evaluate the true genetic value by progeny testing each bull. Many cows must be bred and give birth to offspring. The females must be raised, bred, allowed to give birth and finally milked for a length of time to measure their phenotypic traits.

Furthermore, selection based purely on phenotypic characteristics does not efficiently take into account genetic variability caused by complex gene action and interactions, and the effect of the environmental and developmental variants. There is thus a need for a method of genetically evaluating cattle to enable breeders to more accurately select animals which display desirable phenotypic and the genetic traits.

Genomic selection can lower the high cost of progeny testing currently used to improve sires, since young bull progeny could be evaluated immediately after birth, and young bulls that are determined by genetic testing to have undesirable markers would never be progeny tested or even prior to birth, for the presence/absence of the marker. Traditional thinking is that genome wide markers are the best predictor of overall health and status of animals. Multiple loci located on separate regions of the genome such as different chromosomes can include at least 100, or at least 500, or at least 1000, or at least 5000 or more different loci.

It is an object of the present invention to identify critical traits from the thousands of traits, variation, and genetic markers available for selection and breeding that are highly correlated with successful transition to milk production.

Other objects will become apparent from the description of the invention which follows.

SUMMARY OF THE INVENTION

Historically, production traits such as milk, fat, and protein production have been the emphasis of selection in dairy cattle breeding. More recently, fertility traits and longevity traits have received attention in overall genetic indices used to select dairy cattle. In dairy cattle breeding, little attention has been given to a combination of early lactation infection and metabolic diseases. The present invention provides a way to evaluate the genetic merit of animals for three transition period diseases: mastitis, metritis, and ketosis, which have a disproportionate impact to transition cow health. The resulting evaluation of these traits can be combined into a genetic index to select genetically superior animals. While evaluations of some of these traits are available, other genetic indices that take these into account focusing on transition period health are not available.

The transition period for a dairy cow is from three to two weeks prepartum until two months postpartum. This period is characterized by numerous complex physiological, metabolic, and nutritional changes that interact with each other. It constitutes a turning point in the productive cycle of the cow from one lactation to the next. The manner in which these changes occur and how they are managed are of great importance as they are closely linked to lactation performance, clinical and subclinical postpartum diseases, and reproductive performance that can significantly affect profitability. For instance, the propensity for certain diseases including, for example, displaced abomasum, hypocalcemia, retained placenta, lameness, paratuberculosis, mastitis, metritis and ketosis are elevated during the transition period. The feasibility of evaluating several disease related traits such as displaced abomasum, hypocalcemia, retained placenta, lameness and paratuberculosis were investigated, however, it was determined these traits have limited predictability on the economic impact for producers. Importantly, it was found that genetically evaluating animals for mastitis, metritis, and ketosis was feasible, and relevant. The economic impact to farmers of having cows with lower incidence of these diseases is large, and additionally carries lifelong consequences for all aspects of the health of the cow.

Applicants have developed a method to predictably and reliably prevent multiple metabolic transition cow disorders through the use of genetics, selection and breeding. According to the invention a new selection tool is disclosed which identifies animals, particularly sires whose daughters will be genetically pre-disposed to better health through the transition period. The invention includes methods of using these tools in selection and breeding, as well as resultant populations of animals and progeny populations with improved milk production and transition period health as compared to a population that has not been so selected.

Applicants have identified that three critical phenotypic/genetic measures are highly correlated with transition period health and may be used in selection and breeding protocols and/or in combination with traditional breeding methods to improve predictability of transition period health. According to the invention genetic evaluations for mastitis, ketosis, and metritis have been found to be highly predictive of overall transition health. These evaluations may also be combined with traditional industry evaluations for female calving and fertility traits. The genetic evaluations are produced by directly measuring clinical cases of mastitis, ketosis, and metritis and using compilations of data from ancestors and offspring in selection. Applicant's selection criteria can quickly impact a breeder's population by reducing transition cow disease incidence.

In one embodiment, the present invention provides a method for typing a bovine animal, cell, egg, sperm or embryo comprising determining the number of clinical cases of bovine mastitis, metritis and ketosis within a familial lineage in combination with the evaluation of genetic markers to assign a rating that predicts propensity for the same. The genetic values of the three diseases evaluated are then combined using selection index methodology to determine the weight that each trait should be given. The weights depend on the economic costs of the diseases and on the response to selection achieved in each trait (i.e. how much change in disease incidence do we see if the genetic value of the disease trait change by one point). The identity of the rating may be determined by assessing parental, grandparental, sib or progeny properties through review of thousands of records of real world data.

In a further embodiment, the present invention provides a method for progeny testing of cattle, the method comprising collecting data above and assaying a particular progeny animal.

In another aspect, the present invention relates to a method for selecting a bovine subject for breeding purposes, and/or off-spring therefrom said method comprising determining the propensity of an animal to react favorably to the transition period by screening for mastitis, metritis and ketosis incidence in the lineage of said animal by a method of the invention, and then selecting or not selecting said bovine subject for breeding based on said determined breeding value.

In yet a further embodiment the invention includes selecting animals on the criteria for mastitis metritis and ketosis and breeding those animals, to create a progeny populations of animals with improved transition health and milk production as compared to a populations whose parents have not been so selected.

Still further provided is a method for selectively breeding of cattle using a multiple ovulation and embryo transfer procedure (MOET), the method comprising super ovulating a female animal selected by the above criteria, collecting eggs from said super ovulated female, in vitro fertilizing said eggs from a suitable male animal selected by the above criteria, implanting said fertilized eggs into other selected females allowing for an embryo to develop. In a preferred embodiment, the method is used for selectively breeding dairy cattle, comprising selecting a bull that is favorable for metritis, mastitis and ketosis characteristics and using its semen for fertilizing a selected female animal.

DETAILED DESCRIPTION OF THE INVENTION

In the following description and examples, a number of terms are used. In order to provide a clear and consistent understanding of the description and claims, including the scope to be given such terms, the following definitions are provided for the terms as used in the description and claims. Unless otherwise defined herein, all technical and scientific terms used have the same meaning as commonly understood by one of ordinary skill in the art to which this invention belongs.

Selection and selection criteria: process, model, system or algorithm in order to choose individuals in a population that will contribute genetic material to the next generation. In particular, such a process, model, system or algorithm can be based both on natural or artificial phenomena or procedural steps. Selection criteria can be based on phenotypic or genomic characteristics, for instance, but not limited to, the presence, or degree of presence, of genes, gene expression, genetic markers, combinations of genes, quantitative trait loci, traits or combinations of traits.

Breeding value: the genetic merit of a unit of inheritance such as an individual in a breeding program. This genetic merit is determined by the contribution to at least one phenotypic trait of interest of an individual's gene or genes or (genetic) loci in a breeding program aimed at improving the at least one phenotypic trait of interest.

Estimated breeding value: an approximation of an individual's breeding value, in particular based on the estimated difference between the average performance of that individual's offspring and the average performance of all offspring in a randomly mating population. The estimated average performance of all offspring in a randomly mating population may take into account that individuals with inter-familial relationships, i.e. pedigree relations, normally do not mate.

Genome-wide estimated breeding value: estimated breeding value based on genome-wide information, i.e. information derived from different or remote (genetic) loci of the genome such as loci of different chromosomes. In particular, genome-wide estimated breeding values are an approximation of an individual's genome-wide genetic merit, determined by the contribution to at least one phenotypic trait of interest of an individual's genome-wide genes or genome-wide (genetic) loci, or genome-wide haplotypes or genome-wide molecular marker scores in a breeding program aimed at improving the at least one phenotypic trait of interest.

Genome-wide selection: selection method based on crossing parents with the best genome-wide estimated breeding values per se.

Progeny: as used herein, the term "progeny", refers to the first or further generation obtained by intercrossing.

Phenotype: the composite of an individual's characteristics or traits, particularly observable characteristics or traits, such as, but not limited to morphological, physical, biochemical, developmental or behavioral characteristics or traits. The phenotype of an individual can be formed by the expression of genes as well as environmental factors, and on interactions between gene expression and environmental factors. Phenotypic trait of interest: a heritable characteristic of a plant or animal species which may be quantified in a certain unit of measure. Examples of quantitative phenotypic traits of interest are (but are not limited to): milk yield, milk protein content, carcass weight, fodder conversion, body fat composition, and litter size, coat color, resistances to diseases. It can be desired that a quantitative phenotypic trait of interest is increased or decreased, and the respective shift of the average value for the characteristic in the population can improve the economic value of that population, variety or offspring relative to the parent generation(s).

Genotype: as used herein, the term "genotype" refers to the genetic makeup of a cell, an organism, or an individual (i.e. the specific allele makeup of the individual) usually with reference to a specific character or phenotypic trait of interest under consideration. However, not all organisms with the same genotype necessarily look or act the same way because appearance and behavior are modified by environmental and developmental conditions. Likewise, not all organisms that look alike necessarily have the same genotype.

Genotyping as used herein, the term "genotyping" or "determining the genotype" refers to the process of determining genetic variations among individuals in a species. Single nucleotide polymorphisms (SNPs) are the most common type of genetic variation that are used for genotyping and by definition are single-base differences at a specific locus that is found in more than 1% of the population. SNPs are found in both coding and non-coding regions of the genome and can be associated with a phenotypic trait of interest such as a quantitative phenotypic trait of interest. Hence, SNPs can be used as markers for quantitative phenotypic traits of interest. Another common type of genetic variation that are used for genotyping are "InDels" or insertions and deletions of nucleotides of varying length. For both SNP and InDel genotyping, many methods exist to determine genotype among individuals. The chosen method generally depends on the throughput needed, which is a function of both the number of individuals being genotyped and the number of genotypes being tested for each individual. The chosen method also depends on the amount of sample material available from each individual or sample. For example, sequencing may be used for determining presence or absence of markers such as SNPs, e.g. such as Sanger sequencing and High Throughput Sequencing technologies (HTS). Sanger sequencing may involve sequencing via detection through (capillary) electrophoresis, in which up to 384 capillaries may be sequence analyzed in one run. High throughput sequencing involves the parallel sequencing of thousands or millions or more sequences at once. HTS can be defined as Next Generation sequencing, i.e. techniques based on solid phase pyrosequencing or as Next-Next Generation sequencing based on single nucleotide real time sequencing (SMRT). HTS technologies are available such as offered by Roche, Illumina and Applied Biosystems (Life Technologies). Further high throughput sequencing technologies are described by and/or available from Helicos, Pacific Biosciences, Complete Genomics, Ion Torrent Systems, Oxford Nanopore Technologies, Nabsys, ZS Genetics, GnuBio. Each of these sequencing technologies have their own way of preparing samples prior to the actual sequencing step. These steps may be included in the high throughput sequencing method. In certain cases, steps that are particular for the sequencing step may be integrated in the sample preparation protocol prior to the actual sequencing step for reasons of efficiency or economy. For instance, adapters that are ligated to fragments may contain sections that can be used in subsequent sequencing steps (so-called sequencing adapters). Primers that are used to amplify a subset of fragments prior to sequencing may contain parts within their sequence that introduce sections that can later be used in the sequencing step, for instance by introducing through an amplification step a sequencing adapter or a capturing moiety in an amplicon that can be used in a subsequent sequencing step. Depending also on the sequencing technology used, amplification steps may be omitted.

Genotype/phenotype relationship model: a model that can associate (correlate) genotype with phenotype for individuals in a population. To create such model it is typically required to phenotype individuals of a population and genotype the same individuals. In particular, genotyping can be based on high-density marker data, such as data on the presence or absence of a SNP at a plurality of loci. Likewise, phenotyping can be performed at high accuracy, for example by measuring the value for the quantitative phenotypic trait of interest per individual. The genotype/phenotype relationship model can then be created by calculating correlations between the genotypic data and the phenotypic data. For example, with a dense marker map, such as SNP map, some markers can be correlated with positive or negative effects on a particular quantitative phenotypic trait of interest. In this way, the model can attribute a contribution to the quantitative phenotypic trait of interest to the presence or absence of a marker. Said contribution may for example be expressed in kg, m, L, depending on the unit of measure as used for the quantitative phenotypic trait of interest (for example fruit size, milk production, etc.). Various methods are available in the art in order to construct such a model (Meuwissen et al., 2001).

Locus: as used herein, the term "locus" or "loci" (plural) refers to a specific site (place) or sites on the genome. For example, the "locus" refers to the site in the genome where the two alleles of the locus are found (for diploid organisms). Quantitative trait loci (QTLs) are sites on the genome containing alleles that are associated to a quantitative trait (based on the genotype/phenotype relationship model).

Allele: the term "allele" refers to the nucleotide sequence variant that is present on one of the positions of a particular locus. A diploid individual has two positions for one allele per locus, one position on either one of the two homologous chromosomes. For each of the positions of a particular locus, one or more alternative nucleotide sequence variants may exist in a population, i.e. for each position different possible alleles may exist in a population. However, each individual can have only one of the possible alleles on each one of the positions of a locus. The alternative nucleotide sequence variants, i.e. the different possible alleles, differ at least slightly in nucleotide sequence, and typically can be distinguished based on the presence or absence of at least one SNP or InDel. When referred herein to an "allelic state", reference is made to the presence or absence of an allele at a position within a particular locus, which can be expressed as the presence or absence of the respective marker (e.g. SNP or indel) at the particular locus. Allele dose of a locus: the number of copies present in a genome of a given allele on a given locus. The range for the allele dose is between 0 (no copies present) to the (auto)ploidy level of the genome; i.e. for diploid species, the allele dose for a given allele can be either 0, 1 or 2. For polyploid genomes the max allele dose corresponds to the number of homologous chromosome copies.

Attributed Allele substitution effect: this term refers to the estimated quantitative effect on the trait when on a given locus the one allele (e.g. as measured by presence of a particular SNP) is substituted by the other allele (e.g. as measured by absence of the particular SNP) within a given genetic and/or environmental background. For example, if fruit yield is the quantitative phenotypic trait of interest in a population of plants, the quantitative effect on that trait may be expressed in kg. Based on the genotype/phenotype relationship model, a particular allele on a given locus (e.g. as measured by presence of a particular SNP) can thus be attributed an allele substitution effect of e.g. 0.0001 kg, which means that if the particular allele is replaced by the other possible allele (e.g. as measured by absence of the particular SNP), the quantitative effect on the trait, i.e. fruit yield is estimated to be 0.0001 kg.

Attributed Allele substitution effect corrected for recombination probability: Attributed allele substitution effects can be corrected for recombination probabilities. The further away two loci are from each other, the more likely it is that recombination (crossing over) takes place between the two loci. The distance between loci is measured in terms of recombination probability and is given in cM (centiMorgans; 1 cM is a meiotic recombination probability between two markers of 1%). This is relevant because for both positively and negatively contributing alleles, one would like to know the chance that they are transmitted to offspring. A positive attributed allele substitution effect can be corrected for recombination probability by taking into account the probability that (after crossing with another individual) the allele is transmitted to the genome of offspring. A negative attributed allele substitution effect can be corrected for recombination probability by taking into account the probability that (after crossing with another individual) the allele is not transmitted to the genome of offspring.

Heterozygous and homozygous: as used herein, the term "heterozygous" refers to a genetic condition existing when two different alleles reside at a specific locus, for example a locus having alleles A/B, wherein A and B are positioned individually on either one of the two homologous chromosomes. Conversely, as used herein, the term "homozygous" refers to a genetic condition existing when two identical alleles reside at a specific locus, for example a locus having alleles A/A, positioned individually on either one of the two homologous chromosomes.

Molecular marker technique: as used herein, the term "molecular maker technique" refers to a (DNA based) assay that indicates (directly or indirectly) the presence or absence of a marker allele of interest in an individual (e.g. (crop) plant or cattle). Preferably, it allows one to determine, e.g. by sequencing, whether a particular allele is present or absent at one of the positions at the locus in any individual.

Methods of Screening Animals

The productivity of an individual cow is the sum of the value of the milk she produces, the value of her offspring, and her individual market value when she leaves the herd. Many factors influence individual cow productivity, which is also based on longevity and the proportion of the cow's lifetime spent producing milk. Nonproductive periods include the period from birth until first parturition and dry periods before subsequent calvings. Milk yield is related to stage of lactation. Milk yield increases rapidly after calving, reaches a plateau 40-60 days after calving, and then declines at a rate of 5%-10% per month. The rate of decline is lower in first-parity animals than in older cows. Good reproductive management ensures that the largest proportion of a cow's total lifetime production is spent during early high-producing stages of lactation rather than late, lower-producing periods. Milk yield increases with age and parity until about the sixth lactation; these cows may produce up to 25% more milk volume than first lactation cows. Health disorders or other management problems that reduce longevity have a negative impact on productivity.

The transition period is one of the most critical times in the dairy cow's production cycle. Physiologically, the animal is firstly preparing for, then experiencing, calving and lactation and all the demands that the cow has to deal with. Hormonal changes and a greatly increased demand for energy and nutrients means that the cow must make use of body reserves to meet targets, such as producing milk. Management through the end of the pregnancy and very early lactation has a substantial impact on the cow's ability to respond to these demands without detrimental effects on her health and well-being. The inventors have identified a combination of genetic and phenotypic evaluations which are used to select cows whom are more likely to survive the transition period without developing illnesses or without the need for costly interventions.

Of all of the multiple metabolic, phenotypic and other changes that occur during transition period, Applicants have found that data from the key traits of incidence of metritis, ketosis, and mastitis are the most predictive in determining a cow's ability to thrive during the transition periods. This is surprising as these traits have traditionally been dismissed by most genetic analysis and phenotypic or marker assisted breeding as they have low heritability (i.e. most of the variation of the trait is explained by environmental, rather than genetic, factors). Despite this, Applicant has shown that selection for these traits are highly predictive of overall success through this period and productivity in general. Applicants collected data from dairy herds, compiling millions of records for metritis, ketosis, and mastitis from daughters of over 18,000 dairy sires from herds throughout the world. Applicants accumulated millions of records for each trait. Other traits that we know impact or are impacted by the transition period such as daughter calving traits, somatic cell score, daughter pregnancy rate and cow conception rate may also be used in further embodiments.

Based on these data the animal is given a ranking calculated from all highly reliable sires in the database where 10% of sires receive 5 stars, 20% receive 4 stars, 40% 3 stars, 20% 2 stars, and 10% receive 1 star. The ranking scale is then applied across the dairy sire population so that the highest sires are designated as 5 stars and the lowest as 1 star. In practice of the over 18,000 sires in the database in total, there are approximately 1,800 1 star, 3,600 2 star, 7,200 3 star, 3,600 4 star and 1,800 5 star sires.

Sires without daughters receive a ranking by averaging the breeding value of their parents for Metritis, Mastitis, and Ketosis, or by gnomically evaluating them based on their SNPs. In other embodiments, this may be combined with other genomic evaluations for the other traits. The economic scale ranging from sires at the top end provide a financial gain in efficiency, as well as sires that reduce profitability. The difference between a 1-star and a 5-star sire equates to about a $200 difference for every daughter within the herd for each lactation.

Figure 1:
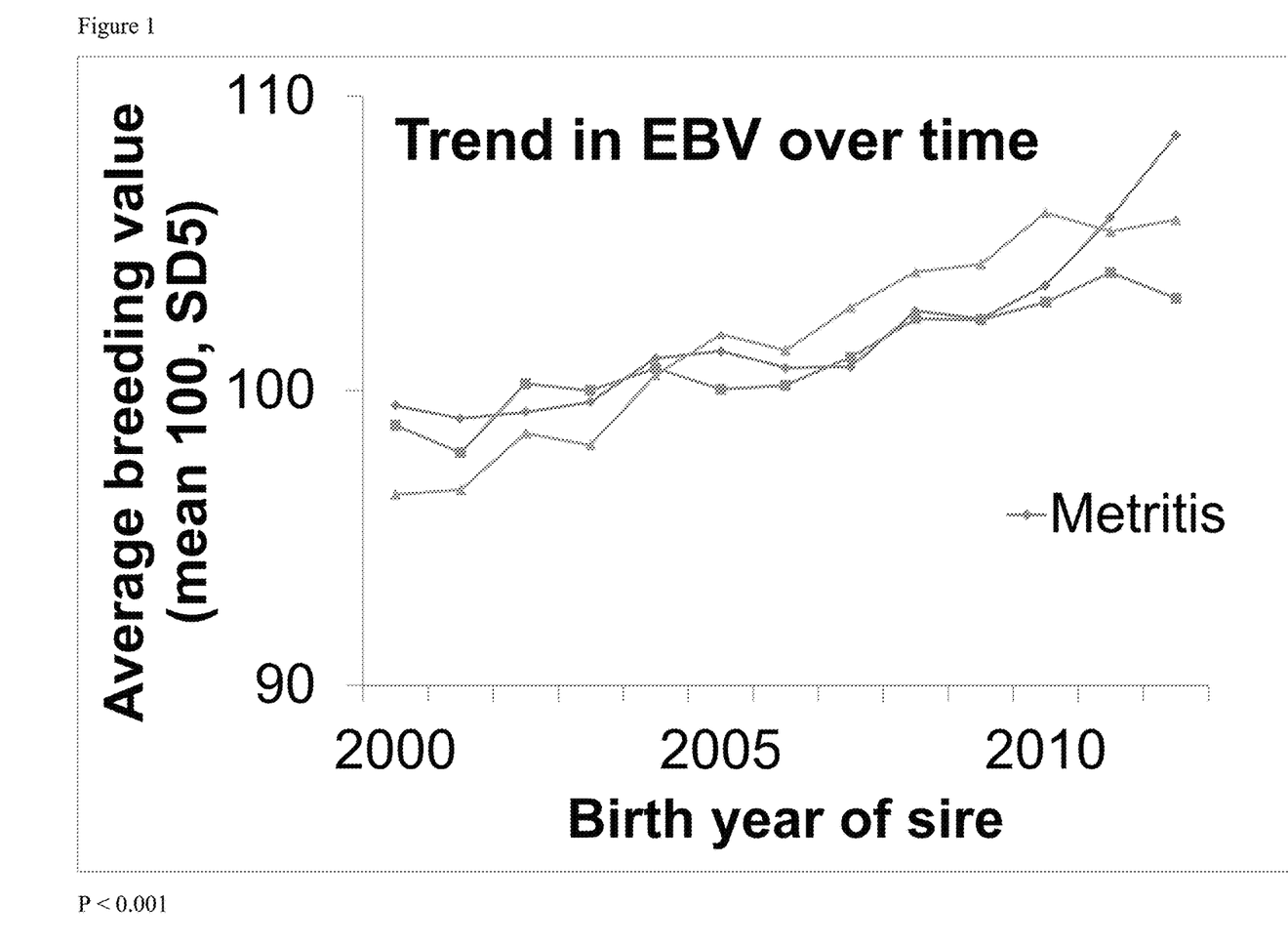
FIG. 1 is a graph showing the trend over time of the estimated breeding value for metritis, mastitis, and ketosis.
Figure 2:
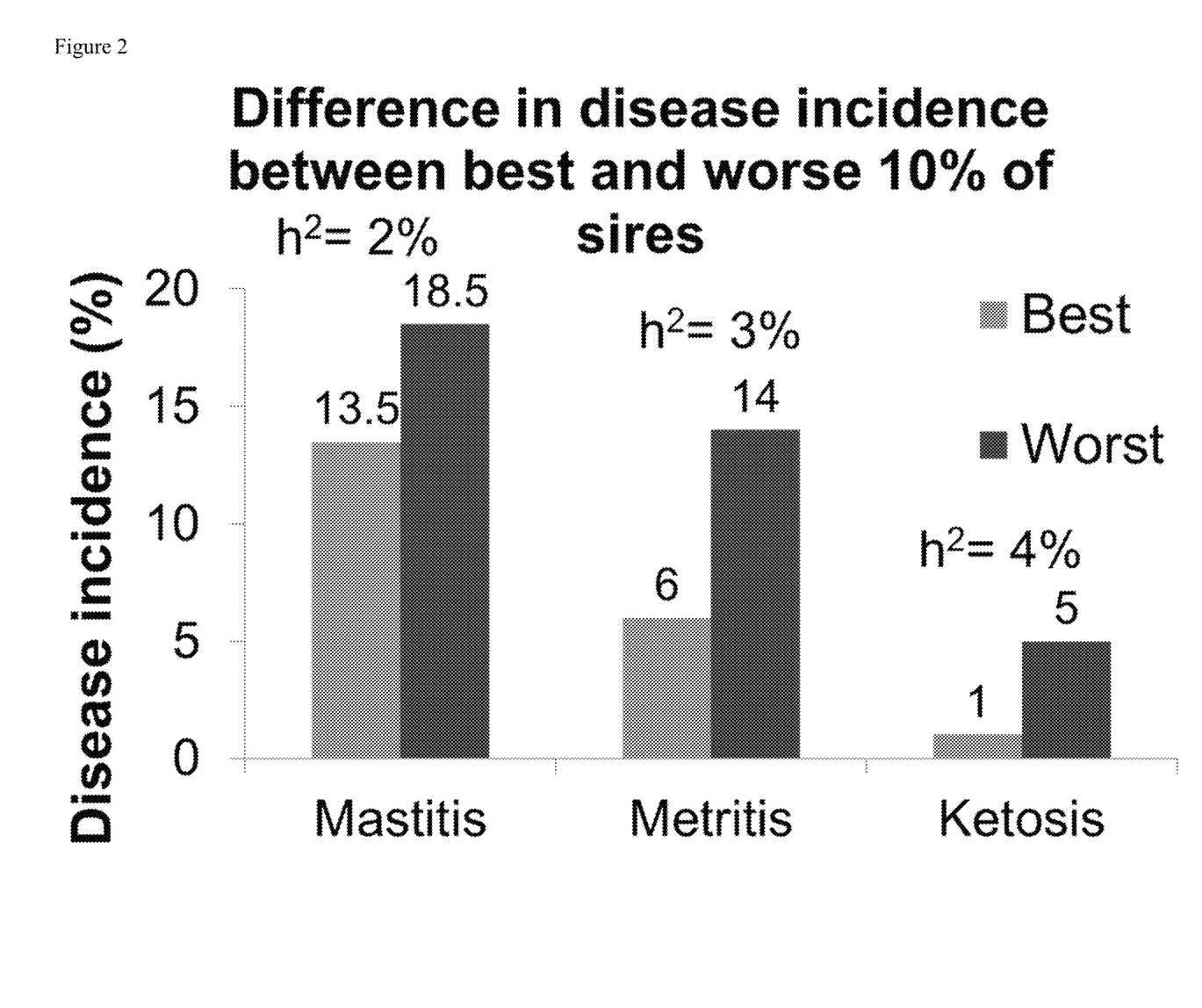
FIG. 2 is a graph showing the difference in disease incidence between the best and worst 10% of sires for mastitis, metritis and ketosis
Figure 3:
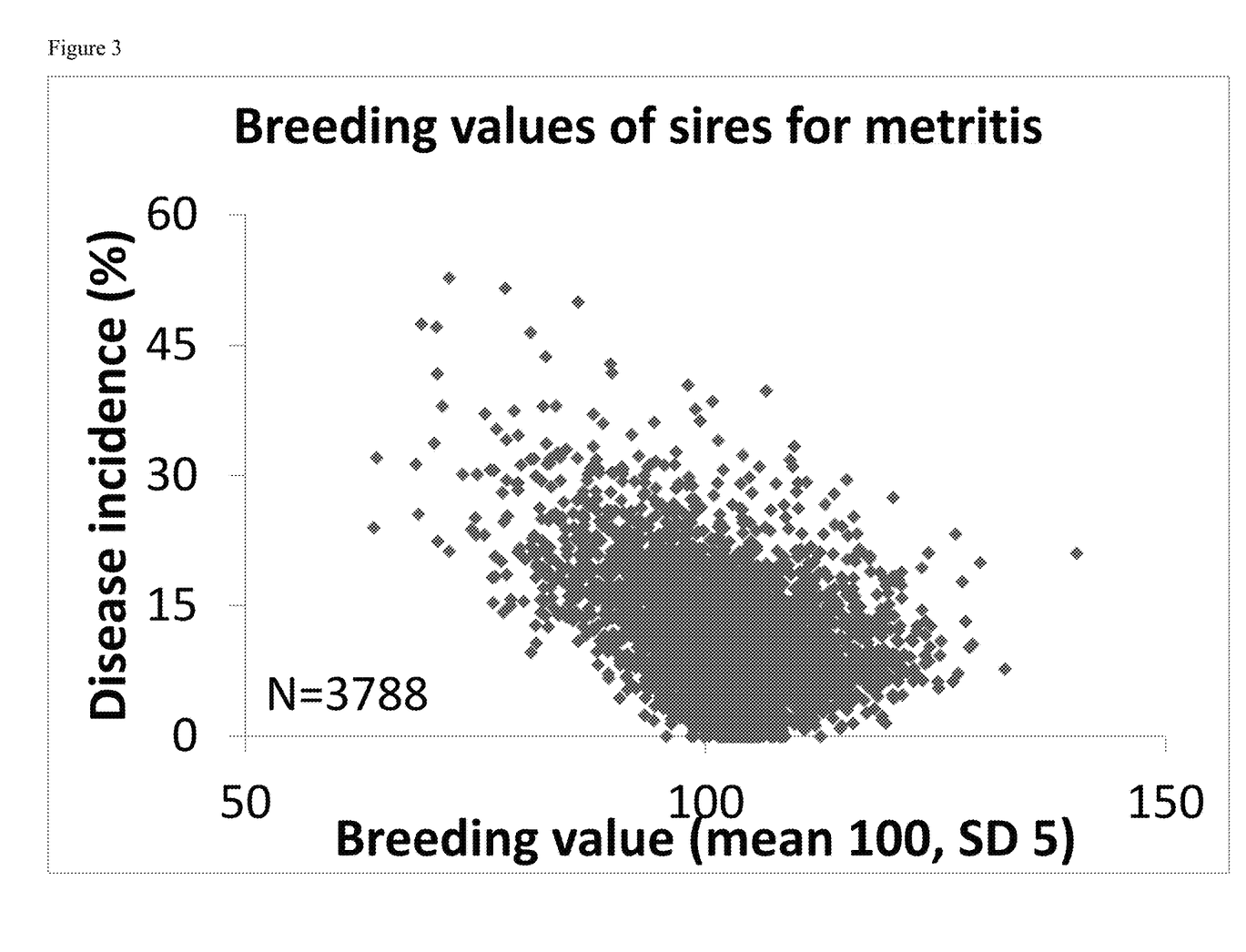
FIG. 3 is a plot showing the breeding value of sires for metritis.
Figure 4:
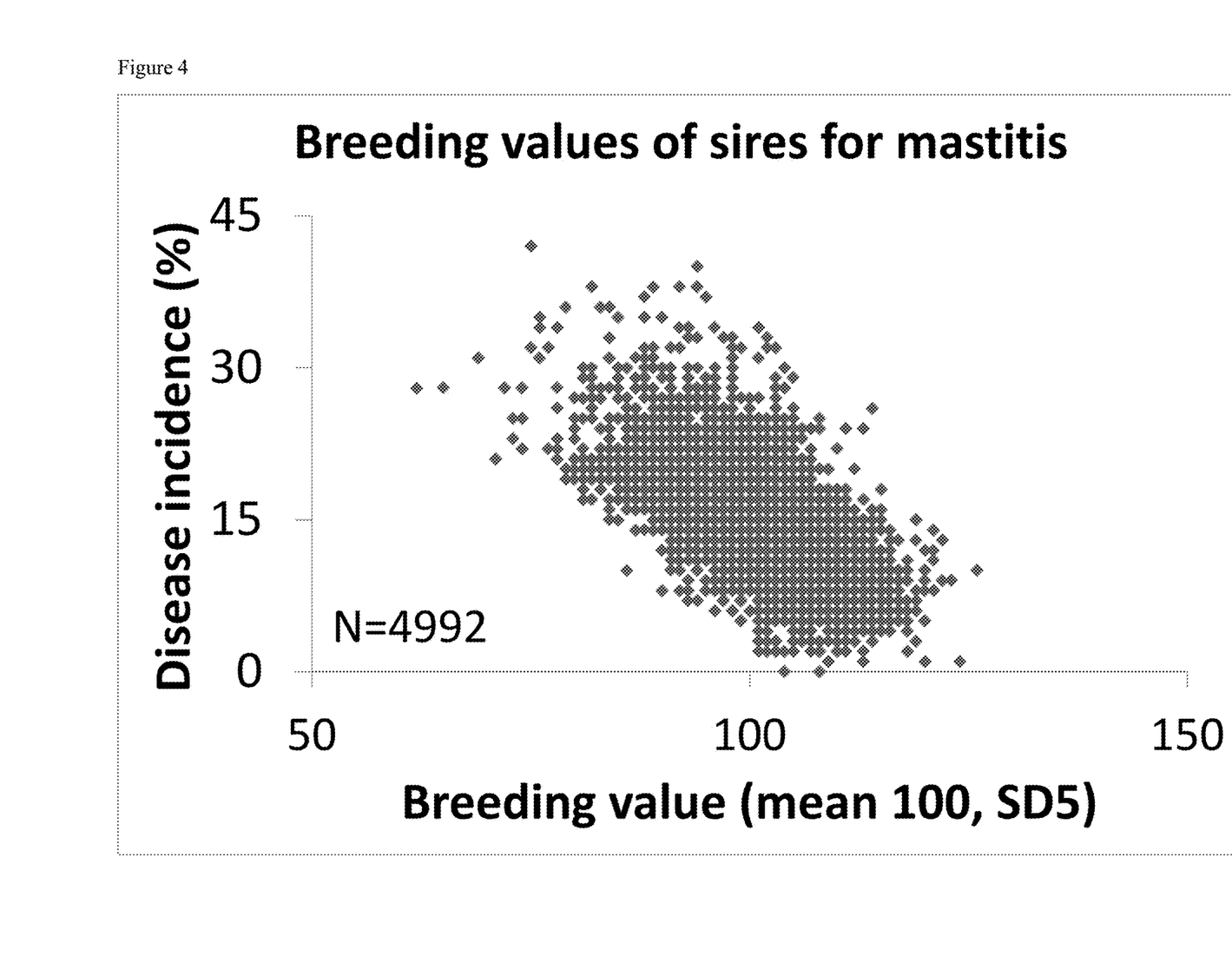
FIG. 4 is a plot showing the breeding value of sires for mastitis.
Figure 5:
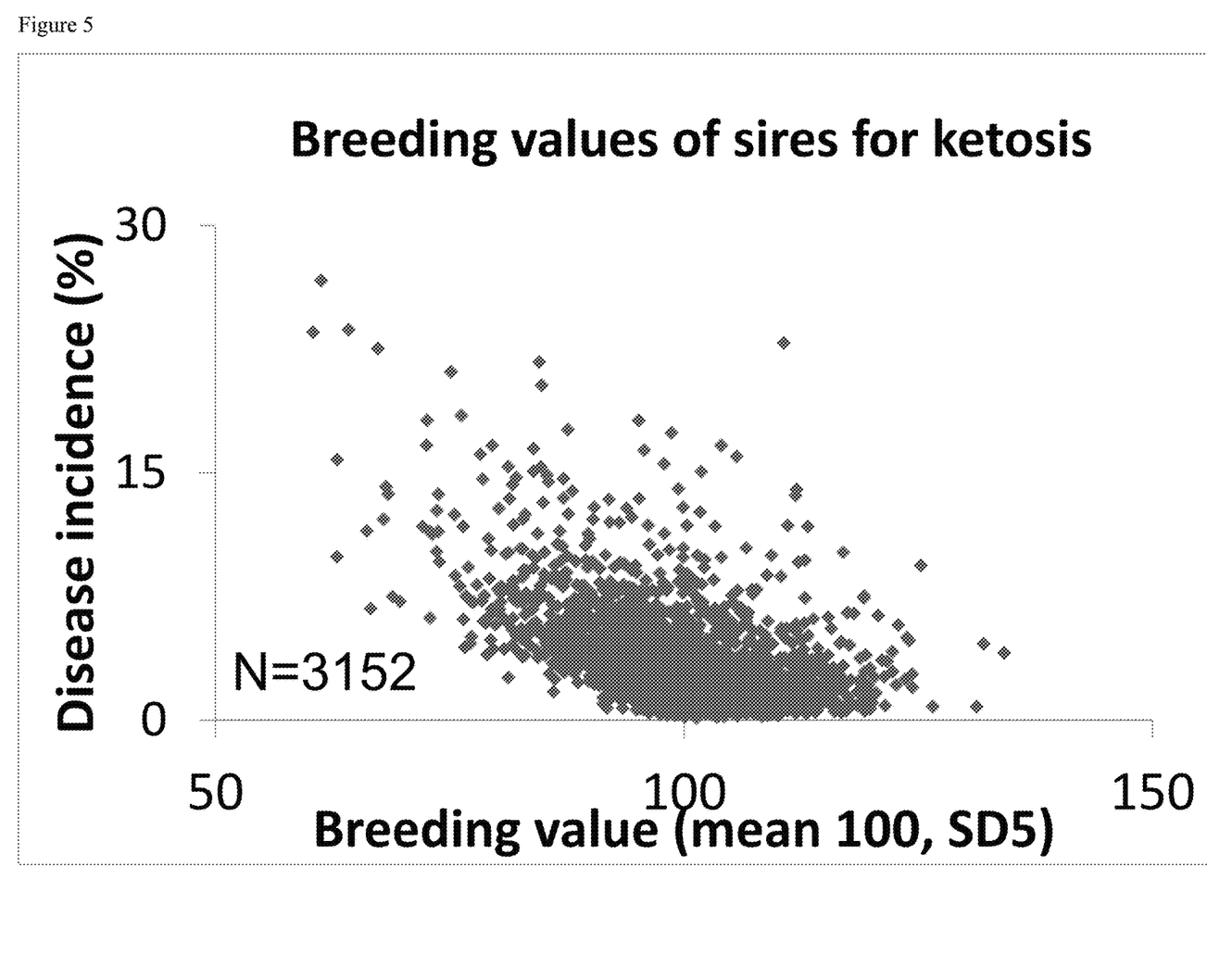
FIG. 5 is a plot showing the breeding values of sires for ketosis.

As seen in FIG. 2 there is much genetic variation to select from in these three traits. For example, out of sires with at least 200 daughters, the best 10% had an average incidence of metritis of 6% in their daughters, while the worst 10% of sires had an average incidence of metritis of 14% in their daughters. A similar pattern is seen in the other two traits. While the heritability ($h^2$) of these traits is low, meaning that most of the variation seen in these traits is explained by non-genetic factors, it is very important that there are real differences between daughters of sires. This variation among sires is what will allow us to change the population in further generations.

According to the invention, the estimated breeding value of these traits correlates highly with net merit of a cow, productive life, and daughter pregnancies (See Examples). Thus these traits are highly predictive of overall transition cow health, even if the disease incidence may not be highly heritable, and importantly there is genetic variation in the population of sires to select on.

In one embodiment, the present invention provides a method for typing a bovine animal, cell, egg, sperm or embryo comprising determining the number of clinical cases of bovine mastitis, metritis and ketosis within a familial lineage in combination with the evaluation of genetic markers to assign a rating that predicts propensity for the same. The identity of the rating may be determined by assessing parental, grandparental or sib properties through review of thousands of records of real world data. In a preferred embodiment this data is combined with other marker data and/or selection criteria based upon estimated breeding value.

In a further embodiment, the present invention provides a method for progeny testing of cattle, the method comprising collecting data above for a particular progeny animal, to ascertain their likelihood of favorable milk production traits, net merit, productive life, and daughter pregnancies.

In another aspect, the present invention relates to a method for selecting a bovine subject for breeding purposes, and/or offspring therefrom said method comprising determining the propensity of an animal to react favorably to the transition period by screening for mastitis, metritis and ketosis incidence in the lineage of said animal by a method of the invention, and then selecting or not selecting said bovine subject for breeding based on said determined breeding value.

In yet a further embodiment the invention includes selecting animals on the criteria for mastitis metritis and ketosis and breeding those animals to create a breeding population or a progeny population of animals with improved transition health and milk production as compared to a populations whose parents have not been so selected.

Still further provided is a method for selectively breeding of cattle using a multiple ovulation and embryo transfer procedure (MOET), the method comprising super ovulating a female animal selected by the above criteria, collecting eggs from said super ovulated female, in vitro fertilizing said eggs from a suitable male animal selected by the above criteria, implanting said fertilized eggs into other selected females allowing for an embryo to develop. In a preferred embodiment, the method is used for selectively breeding dairy cattle, comprising selecting a bull that is favorable for metritis, mastitis and ketosis characteristics and using its semen for fertilizing a selected female animal.

Method of Estimating Breeding Value

The present invention also relates to determination of estimated breeding values. An estimated breeding value (EBV) is an estimate of the genetic merit that an animal will pass down to its offspring. A genetic index (I) is often constructed from a combination of EBV. The EBV and index are estimated on the basis of information of phenotype and genotype values from all possible relatives. A mixed model is used to estimate EBV and multiple linear regression is used to construct the index. The higher the number of relatives and progeny, the better the estimation will be.

In one aspect, the present invention relates to a method for estimating a breeding value in respect of transition period health combined with overall health in a bovine subject, comprising detecting in a sample from said bovine subject the presence or absence of at least one genetic marker that is associated with at least one trait indicative of overall health of said bovine subject and/or off-spring therefrom, wherein said at least one genetic marker is correlated with the same.

The breeding value is in one example determined using a mixed model, for example having the general description of the model in matrix form:

$$y=Xb+Z_a a+e,$$

where: y is a vector with observations on the different traits explained above. The vector b is related to fixed effects, for example age at first calving and herd-year-season of birth whilst vector a contains additive genetic effects related to an animal (the EBV). The matrices X and $Z_a$ are incidence matrices for fixed effects and additive genetic effects, respectively. Vector e contains the residuals of the assayed traits. The covariance components were estimated using ASReml (Gilmour et al., 2014).

In one embodiment, the breeding value is calculated using Best Linear Unbiased Predition (BLUP, Henderson, 1975) or Genomic Best Linear Unbiased Prediction (GBLUP, VanRaden, 2008). Alternatively other methods such as the single-step (Aguilar et al., 2010) or hybrid model (Fernando et al., 2014) may be used. These methods use phenotypes or a combination of phenotype and genotype and apply mixed model methodology to estimate breeding values. Incorporating genotypic information into the breeding value estimate is advantageous because it results in a more accurate estimate. The specific disease resistances traits, genetic markers and marker alleles, samples, bovine subjects, detection methods etc. are known to those of skill in the art and are combined with the metritis, mastitis and ketosis ranking disclosed herein. Genetic evaluations for production traits, including milk, fat, and protein yield, fat and protein percentage, productive life, and somatic cell scores (an indicator of mastitis) are calculated and released to the public three times per year by the Council on Dairy Cattle Breeding. Genetic evaluations for individual bulls may be obtained from the same.

After obtaining EBV for mastitis, metritis, and ketosis, these traits were combined into an economic selection index. Economic values to producers of these disease traits, along with other health and fitness traits were estimated. Using these economic values, as well as estimates of the genetic variation present in the population, selection index methodology was used to determine the weighting factor of the traits in the index. These weights will change periodically as economic values are updated. The novelty lies in that in other genetic indices available to the industry the combination of these three disease traits are not included.

Selective Breeding

In one aspect, the present invention provides a method for selective breeding of bovine subjects. The method of the invention allows the identification of bovine subjects suitable for selective breeding.

In one embodiment these methods comprise the steps of a. providing a bovine subject, b. obtaining a biological sample from said subject, c. determining the presence in that sample of at least one genetic marker indicative of a beneficial train, d. selecting a bovine subject having in its genome said at least one genetic marker, and e. combining said marker data with incidence and ranking for mastitis, metritis and ketosis to identify a favorable subject and f using said bovine subject for breeding.

The biological sample could be any suitable sample comprising genetic material, and which is preferably easily obtainable. Sample types are described further elsewhere herein. The bovine is preferably a male subject, i.e. a bull. For example, when the bovine subject is a bull, the use of the bovine subject for breeding would normally include collecting semen from said bull and using said semen for artificial insemination of one or more heifers or cows. However, the presence of the relevant genetic marker(s) may also be determined in cows and heifers according to the method of the invention.

In another preferred embodiment, the population of individuals is of a species selected from the group consisting of Cattle (*Bos taurus, Bos indicus*), Water buffalo (*Bubalus bubalis*), Equine (*Equus caballus*), Sheep (*Ovis aries*), Goat (*Capra hircus*), Pig (*Sus scrofa*), Rat (*Rattus novergicus*), Mouse (*Mus musculus*), Cat (*Felis catus*), Dog (*Canis familiaris*), Rabbit (*Oryctolagus cuniculus*), and Guinea pig (*Cavia porcellus*).

As described earlier herein, it is also envisaged that the present method may comprise of (enabling) intercrossing (or interbreeding) of members of the selected combination of traits, such that offspring, i.e. a next generation is obtained. In addition, it is also envisaged that the resulting offspring as obtained is intercrossed.

Further provided is a method for selectively breeding of cattle using a multiple ovulation and embryo transfer procedure (MOET), the method comprising superovulating a female animal, collecting eggs from said superovulated female, in vitro fertilizing said eggs from a selected suitable male animal, implanting said fertilized eggs into other females and allowing for an embryo to develop.

In a preferred embodiment, the method is used for selectively breeding dairy cattle, comprising selecting a bull that is favorable for milk production traits as described herein and optionally other genetic markers, and using its semen for fertilizing a female animal. More preferably, the female animal which is also favorable for said traits and optional genetic markers. MOET procedure may be preferably used for the selective breeding.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims. Thus, many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims.

The following examples are offered by way of illustration and not by way of limitation.

Example 1

The objective of this study was to develop a genetic evaluation of mastitis (MAST), metritis (MET), and ketosis (KET) from producer recorded data. The period from calving to 60 days post-partum is one of the most challenging times in a cow's lactation when up to 75% of diseases occur. Dairy producers routinely collect health data for management purposes, and these data are also valuable for genetic evaluation. Limited genetic evaluation of these traits exists. Data from on farm management systems was mined by finding keywords that would indicate that a cow had a case of one of the diseases. Only cases within the first 60 days of a cow's first lactation were used. A total of U.S. Pat. Nos. 3,264,415, 2,822,312, and 2,035,174 observations from first lactation Holsteins coming from 776, 593, and 421 farms were used in the evaluations of MAST, MET, and KET, respectively. ASReml was used to fit a linear sire model with an eight generation pedigree. For each trait a mean as well as herd-year-season of calving and age at first calving were fitted as fixed effects. The random genetic effect of sire was used for all traits. The mean first lactation disease incidence was 16%, 10%, and 3% for MAST, MET, and KET, respectively. The heritability of MAST, MET, and KET was 2%, 4%, and 3%, respectively. There was genetic variation between the best 10% and the worst 10% of sires by EBV. On average the disease incidences of the bottom 10% of sires was higher than the incidences of the top 10% of sires by 5%, 8%, 4% for MAST, MET, and KET, respectively. MAST, MET, and KET have a large economic impact on dairies, and selecting sires whose daughters have lower disease incidence is a cost effective way to make cumulative and permanent change in the population. Given the low heritability of these traits and the wide array of economically relevant traits in dairy, these should be incorporated into a selection index to achieve healthier transition cows.

Data from on farm management software was mined by finding keywords that indicate a case of MAST, MET, or KET. Only cases within the first 60 days of a cow's first lactation were used.

A total of U.S. Pat. Nos. 3,264,415, 2,822,312, and 2,035,174 observations from first lactation Holsteins coming from 776, 593, and 421 farms were used for MAST, MET, and KET, respectively.

ASReml (Gilmour et al., 2014) was used to fit a linear sire model with an eight generation pedigree. Fixed effects were an overall mean, herd-year-season of calving, and age at first calving. Sire was fitted as a random genetic effect.

| Genetic correlation of EBV with other traits (P < 0.01) | | | |
|---|---|---|---|
|  | Mastitis | Metritis | Ketosis |
| Milk | −0.10 | 0.06 | −0.02 |
| Fat | 0.06 | 0.11 | 0.04 |
| Protein | −0.03 | 0.16 | 0.08 |
| Net Merit | 0.40 | 0.30 | 0.22 |
| Somatic cell score | −0.66 | −0.11 | −0.14 |
| Productive life | 0.52 | 0.29 | 0.27 |
| Daughter preg. | 0.32 | 0.33 | 0.27 |
| Type | 0.22 | 0.02 | 0.08 |
| Udder composite | 0.32 | 0.04 | 0.12 |

MAST, MET, and KET have a large economic impact on dairies, and selecting sires whose daughters have lower disease incidence is a cost effective way to make cumulative and permanent change in the population. Given the low heritability of these traits and the wide array of economically relevant traits in dairy, these are surprisingly predictive.

Example 2

Star Ranking and Phenotypes.

| Sire ranking | metritis incidence | ketosis incidence |
|---|---|---|
| ***** | 26% | 6% |
| **** | 30% | 12% |
| *** | 30% | 12% |
| ** | 37% | 23% |
| ** | 39% | 23% |

One can see that using the selection scheme of the invention, one can predict an animal will have reduced metritis incidence by 13% and ketosis by 17%.

REFERENCES

1. Meuwissen, T. H. E., Hayes B. J., Goddard, M. E., Prediction of Total Genetic Value Using Genome-Wide Dense Marker Maps, Genetics (2001) vol. 157 no. 4 1819-1829.
2. Gilmour, A. R., Gogel, B. J., Cullis, B. R., Welham, S. J. and Thompson, R. ASReml User Guide Release 4.0 VSN International Ltd, Hemel Hempstead, HP1 1ES, (2014) UK.
3. VanRaden P M: Efficient methods to compute genomic predictions. J Dairy Sci. 2008, 91: 4414-4423. 10.3168/jds.2007-0980.
4. Aguilar, I. et al. Hot topic: A unified approach to utilize phenotypic, full pedigree, and genomic information for genetic evaluation of Holstein final score. Journal of Dairy Science, Volume 93, Issue 2, 743-752.
5. Fernando, R. L., J. C. M. Dekkers and D. J. Garrick. A class of Bayesian methods to combine large numbers of genotyped and non-genotyped animals for whole-genome analyses. (2014) Genet. Sel and Evol. 46:50 doi:10.1186/1297-9686-46-50.
6. Henderson, C. R. (1975). "Best linear unbiased estimation and prediction under a selection model". Biometrics 31 (2): 423-447. doi:10.2307/2529430. JSTOR 2529430. PMID 1174616.

What is claimed is:

1. A method of breeding bovine animals to create a progeny population with improved milk production and health during the transition period comprising:
   a) detecting in a sample from at least one bovine subject of a population the presence or absence of at least one genetic marker associated with mastitis, at least one genetic marker associated with metritis, and at least one genetic marker associated with ketosis;
   b) assigning an estimated breeding value to said bovine subject based on the presence or absence of said genetic markers;
   c) selecting a bovine animal ranked within the top 30% of the population based on said estimated breeding value, wherein the selected bovine animal is used as a first parent bovine animal; and
   d) breeding said first parent bovine animal with a second parent bovine animal to create said progeny population, wherein female bovine animals of said progeny population demonstrate improved milk production and health during the transition period when compared to female bovine animals of a progeny population where a first parent bovine animal has not been so selected.

2. The method of claim 1, wherein said first parent bovine animal is a dam.

3. The method of claim 1, wherein said first parent bovine animal is a sire.

4. The method of claim 1, wherein both the first parent bovine animal and the second parent bovine animal are ranked within the top 30% of the population based on said estimated breeding value.

5. The method of claim 1, wherein said first parent bovine animal is ranked within the top 10% of bovine animals of the population based on said estimated breeding value.

6. The method of claim 1, wherein said first parent bovine animal is ranked within the top 20% of bovine animals of the population based on said estimated breeding value.

7. The method of claim 1, wherein said estimated breeding value is combined with estimated breeding values for milk, fat, and protein yield, fat and protein percentage, productive life, and/or somatic cell scores.

8. A method of selecting a breeding population of bovine comprising:
   detecting in samples from multiple bovine subjects the presence or absence of at least one genetic marker associated with mastitis, at least one genetic marker associated with metritis, and at least one genetic marker associated with ketosis;
   selecting at least one bovine subject ranked within the top 30% of the multiple bovine subjects based on the presence or absence of the genetic markers; and
   breeding said selected bovine subject to create a progeny population, wherein said progeny population has an improved milk production and health, particularly during the transition period when compared to a progeny population where the animal has not been so selected.

9. The method of claim 8 wherein said at least one selected bovine subject is a dam.

10. The method of claim 8 wherein said at least one selected bovine subject is a sire.

11. The method of claim 8 wherein said at least one selected bovine subject comprises both a dam and a sire.

12. The method of claim 8 wherein said at least one selected bovine subject is ranked within the top 10% of the multiple bovine subjects based on the presence or absence of the genetic markers.

13. The method of claim 8 wherein said at least one selected bovine subject is ranked within the top 20% of the multiple bovine subjects based on the presence or absence of the genetic markers.

14. The method of claim 8 wherein said metritis, mastitis and ketosis incidence is assigned an estimated breeding value.

15. The method of claim 14 wherein said estimated breeding value is combined with estimated breeding values for other traits such as milk, fat, and protein yield, fat and protein percentage, productive life, and somatic cell scores.

16. A progeny population produced by the method of claim 8.

17. A method for selectively breeding bovine animals using a multiple ovulation and embryo transfer procedure (MOET) procedure, the method comprising:
   superovulating a first female bovine animal selected according to the method of claim 1,
   collecting eggs from said superovulated first female bovine animal,
   in vitro fertilizing said collected eggs from a suitable male bovine animal, implanting said fertilized eggs into other a second female bovine animal and allowing for an embryo to develop from said implanted fertilized egg to create a population of male and female bovine progeny animals, wherein said female bovine progeny animals have improved milk production and health, particularly during the transition period when compared to a female bovine animal of a progeny population where the first female bovine animal has not been so selected.

18. The method of claim 1, wherein said breeding comprises:
   collecting semen from said first parent bovine animal; and
   using said semen for fertilizing said second parent bovine animal.

19. The method according to claim 18, wherein the second parent bovine animal is in-vitro fertilized.

20. The method according to claim 18, wherein a Multiple Ovulation and Embryo Transfer (MOET) procedure is used.

* * * * *

UNITED STATES PATENT AND TRADEMARK OFFICE
CERTIFICATE OF CORRECTION

| | |
|---|---|
| PATENT NO. | : 11,690,361 B2 |
| APPLICATION NO. | : 16/445832 |
| DATED | : July 4, 2023 |
| INVENTOR(S) | : Katrina Dattilo et al. |

It is certified that error appears in the above-identified patent and that said Letters Patent is hereby corrected as shown below:

On the Title Page

<u>Column 1, (71) Applicant</u>
DELETE: "GENUS PLC, DeForest, WI (US)"
INSERT: --ABS GLOBAL, INC., DeForest, WI (US)--

Signed and Sealed this
Fifteenth Day of August, 2023

Katherine Kelly Vidal
*Director of the United States Patent and Trademark Office*